US011376357B2

(12) United States Patent
Aarestad et al.

(10) Patent No.: US 11,376,357 B2
(45) Date of Patent: Jul. 5, 2022

(54) MEDICAL PUMP FILTRATION DEVICE, AND METHODS OF MANUFACTURE AND USE THEREOF

(71) Applicant: SOMMETRICS, INC., Vista, CA (US)

(72) Inventors: Jerome K. Aarestad, Escondido, CA (US); William C. Paul, III, La Mesa, CA (US); Stephen G. T. Maine, Los Angeles, CA (US)

(73) Assignee: SOMMETRICS, INC., Vista, CA (US)

( * ) Notice: Subject to any disclaimer, the term of this patent is extended or adjusted under 35 U.S.C. 154(b) by 655 days.

(21) Appl. No.: 15/551,882

(22) PCT Filed: Feb. 17, 2016

(86) PCT No.: PCT/US2016/018320
§ 371 (c)(1),
(2) Date: Aug. 17, 2017

(87) PCT Pub. No.: WO2016/134052
PCT Pub. Date: Aug. 25, 2016

(65) Prior Publication Data
US 2018/0028728 A1    Feb. 1, 2018

Related U.S. Application Data

(60) Provisional application No. 62/184,799, filed on Jun. 25, 2015, provisional application No. 62/117,313, filed on Feb. 17, 2015.

(51) Int. Cl.
*A61M 1/00*    (2006.01)
(52) U.S. Cl.
CPC ............ *A61M 1/962* (2021.05); *A61M 1/784* (2021.05); *A61M 2205/3306* (2013.01);
(Continued)

(58) Field of Classification Search
CPC ................ A61M 1/009; A61M 1/0052; A61M 2205/75; A61M 2205/3306;
(Continued)

(56) References Cited

U.S. PATENT DOCUMENTS

| 5,343,878 A | 9/1994 | Scarberry et al. |
| 6,942,634 B2 | 9/2005 | Odland |

(Continued)

FOREIGN PATENT DOCUMENTS

| JP | 2013538071 A | 10/2013 |
| WO | 2013149078 A1 | 10/2013 |

(Continued)

OTHER PUBLICATIONS

International Search Report and Written Opinion dated May 2, 2016, in PCT/US2016/018320 (9 pages).

(Continued)

*Primary Examiner* — Nicholas J. Weiss
*Assistant Examiner* — Alessandro R Del Priore
(74) *Attorney, Agent, or Firm* — Acuity Law Group, PC; Michael A. Whittaker

(57) ABSTRACT

The present invention relates to medical vacuum pump filtration devices configured to filter air being received by the pump. The filtration devices comprise a pump housing and a mounting cap which incorporates filtration capabilities that capture and or divert particulate matter and moisture away from a pump intake opening. The filtration cap can also include apertures for sensors contained within the vacuum pump housing and the filtration cap. Compliance features that ensure proper installation and use of the filtration device can be included.

22 Claims, 7 Drawing Sheets

(52) U.S. Cl.
CPC ............... *A61M 2205/3334* (2013.01); *A61M 2205/3337* (2013.01); *A61M 2205/584* (2013.01); *A61M 2205/6054* (2013.01); *A61M 2205/6063* (2013.01); *A61M 2205/75* (2013.01); *A61M 2205/7536* (2013.01); *A61M 2205/8206* (2013.01); *A61M 2207/00* (2013.01)

(58) Field of Classification Search
CPC .. A61M 2205/3334; A61M 2205/3337; A61M 2205/584; A61M 2205/6054; A61M 2205/8206; A61M 2207/00; A61M 2205/7536; A61M 2205/705; A61M 2205/6072; A61M 2205/6063
See application file for complete search history.

(56) References Cited

U.S. PATENT DOCUMENTS

| | | | |
|---|---|---|---|
| 7,182,082 B2 | 2/2007 | Hoffrichter | |
| 7,534,240 B1 | 5/2009 | Johnson | |
| 7,762,263 B2 | 7/2010 | Aarestad | |
| 8,734,410 B2 | 5/2014 | Hall et al. | |
| 9,820,881 B2 | 11/2017 | Aarestad et al. | |
| 2005/0209547 A1* | 9/2005 | Burbank | A61L 2/0017 604/5.01 |
| 2007/0265585 A1 | 11/2007 | Joshi et al. | |
| 2008/0015469 A1 | 1/2008 | Morton et al. | |
| 2008/0135725 A1* | 6/2008 | Bisch | A61M 5/14232 250/206 |
| 2009/0240218 A1* | 9/2009 | Braga | A61M 1/784 604/313 |
| 2011/0196321 A1* | 8/2011 | Wudyka | A61M 1/784 604/319 |
| 2011/0257612 A1* | 10/2011 | Locke | A61F 13/02 604/319 |
| 2011/0283884 A1* | 11/2011 | Larsen | A61M 16/0808 95/25 |
| 2012/0016323 A1* | 1/2012 | Coulthard | A61M 1/0088 604/319 |
| 2013/0331823 A1* | 12/2013 | Askem | F04B 53/10 417/44.1 |
| 2014/0155847 A1* | 6/2014 | Neatrour | A61M 1/79 604/319 |
| 2014/0171920 A1* | 6/2014 | Smith | A61F 13/0216 604/540 |
| 2014/0144450 A1 | 9/2014 | Böhm et al. | |
| 2015/0057625 A1* | 2/2015 | Coulthard | A61F 13/0206 604/319 |
| 2017/0136178 A1* | 5/2017 | Kamen | A61M 5/16831 |

FOREIGN PATENT DOCUMENTS

| | | |
|---|---|---|
| WO | 2013/171585 A9 | 11/2013 |
| WO | 2013182978 A1 | 12/2013 |
| WO | 2014151930 A2 | 9/2014 |

OTHER PUBLICATIONS

The Extended European Search Report and Written Opinion issued in EP 16753001 dated Aug. 7, 2018 (8 pages).
Czech and Kowalczyk, Pressure-Sensitive Adhesives for Medical Applications, in Wide Spectra of Quality Control, 2011:309-332.
The Office Action issued by the JPO in JP Patent Applicaiton No. 2017-542474 dated Jan. 21, 2020—incl Engl lang transl (11 pages total).
The Office Action issued by the JPO in JP Patent Applicaiton No. 2017-542474 dated Mar. 2, 2021—incl Engl lang transl (4 pages total).

* cited by examiner

MEDICAL PUMP FILTRATION DEVICE, AND METHODS OF MANUFACTURE AND USE THEREOF

The present invention is filed under 35 U.S.C. § 371 as the U.S. national phase of International Patent Application No. PCT/US2016/018320, filed Feb. 17, 2016, which designated the U.S. and claims the benefit of priority to U.S. Provisional Application No. 62/117,313 filed Feb. 17, 2015, and to U.S. Provisional Application No. 62/184,799 filed Jun. 25, 2015, each of which is hereby incorporated in its entirety including all tables, figures, and claims.

BACKGROUND OF THE INVENTION

The following discussion of the background of the invention is merely provided to aid the reader in understanding the invention and is not admitted to describe or constitute prior art to the present invention.

The external application of negative pressure to patients for palliative or therapeutic purposes is well established in the medical arts.

In one example, U.S. Pat. No. 7,534,240 relates to an apparatus for performing "negative pressure wound therapy" ("NPWT"), also known as topical negative pressure, sub-atmospheric pressure dressings or vacuum sealing technique. NPWT is a therapeutic technique used to promote healing in acute or chronic wounds, fight infection and enhance healing of burns. A vacuum source is used to create sub-atmospheric pressure in the local wound environment. A dressing, containing a drainage tube, is fitted to the contours of a deep or irregularly-shaped wound and sealed with a transparent film. The tube is connected to the vacuum source, which purports to turn an open wound into a controlled, closed wound while removing excess fluid from the wound bed to enhance circulation and remove waste.

In another example, U.S. Pat. Nos. 5,343,878, 7,182,082, and 7,762,263 describe various devices which purport to utilize external application of negative pressure upon the external neck surface of patients. A therapeutic appliance is typically provided that has a surface which is configured to enclose an external area of the throat (the term "throat" as used herein referring to the anterior portion of the neck extending approximately from the chin to the top of the sternum and laterally to a point posterior to the external jugular vein) overlying a portion of the upper respiratory passage. In certain embodiments, these appliances can provide a chamber (e.g., a hollow space filled with air molecules) lying between the surface and the throat. The therapy appliance is operably connected to an air pump which is configured to produce a partial vacuum in this chamber.

These "negative pressure" therapeutic apparatuses and methods have in common a requirement for some apparatus (e.g., an "air pump") to create and maintain the differential negative pressure (relative to atmospheric pressure for example) at the desired location on the patient. Success of these negative pressure therapies is reliant on the consistent function of the vacuum pump. However, complexities in the field of pump design and operation exist including the fouling by particulate matter and moisture. This ultimately causes an abridged lifespan of the pump and failure.

BRIEF DESCRIPTION OF THE INVENTION

It is an object of the invention to provide a filtration device that is configured to releasably engage with the air input surface of a medical vacuum pump and to thereby provide a replaceable filter element to prevent contamination of the pump by matter in the input air flow.

In various aspects described below, the filtration device can be in the form of a cap element which provides a mating surface configured to provide a friction fit with a corresponding receiving surface on the pump housing element. In certain embodiments, the mating surface and the receiving surface create a sandwich seal with a chamber structure that forms the vacuum chamber on the patient. A filter, and preferably a hydrophobic filter, is supported by the filtration cap element.

In certain aspects, one or more recognition features are present on the filtration cap element, the pump housing element or both, which provide a means to identify that the appropriate cap element is installed to the pump housing element. As used herein a recognition feature may include any features used to identify and ensure compatibility of the filtration cap element and the pump housing element.

The term "filtration cap element" refers to a discrete element of a filtration device which comprises a filter membrane and which is designed as a disposable component which mates with a pump housing element preferably designed for multiple uses. As used herein, the term "disposable" with regard to the filtration cap element refers to the characteristic that the filtration cap element may be disengaged from the pump housing element in the course of normal use by the user of the system such that the electronics present in the pump housing element may be easily separated from, and need not be discarded with, the filtration cap element. This can serve to place the device components of the system most susceptible to wear and cleanability issues on a disposable unit, while retaining the more expensive electronic components on an easily cleanable and reusable unit.

The term "pump housing element" refers to a discrete element of a filtration device which comprises a vacuum source configured to create a desired level of vacuum within an enclosure positioned at a location on the exterior of the human body. The pump housing may be, but need not be, unitary with the enclosure.

The term "pump housing exterior cap" refers to a discrete element of the filtration device which comprises a cap configured to affix to the exterior of the vacuum pump housing and enclose components mounted therein. The pump housing cap may contain apertures to serve as exhaust ports for the pump element and may be mounted releasable or affixed permanently to allow servicing or prevent user tampering respectively.

The term "vacuum system" or "vacuum pump filtration system" as used herein refers to an integral system comprising a filtration cap element, a pump housing element, and an enclosure, where the enclosure is configured to mate with a portion of the human body and thereby create a chamber; the pump housing element is configured to support a vacuum pump and its associated electronics in a manner configured to create a vacuum within the chamber; and the filtration cap element is configured to position a filter membrane between the interior of the chamber and the vacuum pump such that air being removed from within the chamber must pass through the filter membrane prior to reaching the vacuum pump.

In certain aspects, one or more tangs or tabs are present on the filtration cap element, the pump housing element, or both, which provide one or more guidance feature(s) to ensure a proper orientation of mating between the two elements. In preferred embodiments, one or more of these tangs can be utilized as part of a sensor system to determine various parameters related to use of the filtration device. These parameters can include, but are not limited to, compatibility of the particular filtration device with the pump housing element (e.g., acting as a recognition feature), correct placement of the filtration device, usage time of a particular filtration device, and user compliance with a prescribed medical use. This list is not meant to be limiting. Moreover, these data aspects may be performed by elements of the device other than the guidance tang(s) as described hereinafter.

The guidance tang(s) may also participate in other functions regarding the mating of a cap element with a corresponding pump element. For example, one or more tangs may trigger a pump "activation switch", without which triggering the pump may not be energized. In this manner, the vacuum pump is prevented from operating without the presence of a compatible filtration device, thereby preventing inadvertent fouling of the pump mechanism. This list is again not meant to be limiting, and these data aspects may be performed by elements of the device other than the guidance tang(s) as described hereinafter.

By way of example, the filtration cap element may contain a tang that is located on the interior surface the filtration cap element and which, upon installation of the filtration cap element to the pump housing element, extends into the pump housing element to a functional depth. As defined herein a "functional depth" refers to a depth of penetration into the pump housing element that satisfies conditions associated with correct installation of the filtration cap element. This includes, but is not limited to, proper orientation and or proper mating of the filtration cap element to the pump housing element.

In another aspect one or more tangs present on the filtration cap element may be used to releasably attach the filtration cap element to the pump housing element by mating with a corresponding tang acceptance feature. In a preferred embodiment, a plurality of tangs are situated around the interior surface of the filtration cap element in an asymmetric pattern, and correspond to an asymmetric pattern of acceptance features in the form of depressions on the pump housing element. Such elements can serve to secure the filtration cap element to the pump housing element, while ensuring a desired orientation of the filtration cap element relative to the pump housing element.

In a further aspect, the device contains mounting surfaces and or recesses for mounting and or the receiving of components and features. In an embodiment of the invention the pump housing element contains asymmetric recesses on its outer surface nearest to the mating surface of the filtration cap element corresponding to the asymmetric tangs on the filtration cap element so that when the filtration cap element is installed the recesses align with the tangs and the cap installs on the pump housing element in the desired orientation.

In another aspect one or more tangs present on the exterior element may be used to releasably attach the exterior cap element to the pump housing element by mating with a corresponding tang acceptance feature. In a preferred embodiment, a plurality of tangs are situated around the rim of the exterior cap element in an asymmetric pattern, and correspond to an asymmetric pattern of acceptance features in the form of depressions on the pump housing element. The attaching features can be interchangeable, for example tangs present on the pump housing and recesses present on the exterior cap. Such elements can serve to releasable secure the exterior cap element to the pump housing element, during use or assembly prior to gluing or welding while ensuring a desired orientation of the exterior cap element relative to the pump housing element.

In a further aspect the tang(s) and or mounting surface(s) and or recess(es) may be shaped in a manner as to bias the direction in which a component is to be mounted. For example the tang or recess may be tapered/slightly offset to frictionally force the cap downward when installed. The angle of the offset creates a rate and a downward force pushing the filtration cap element onto the pump intake surface and subsequently minimizes gaps between the intake surface of the pump and the filtration cap element. As used herein the term offset is defined as a sloping ledge in a feature where the thickness of the part above is less, for example an angled tang.

The pump housing element and the filtration cap element may each be made of a generally rigid material. The term "generally rigid" as used herein refers to a material which is sufficiently rigid to maintain the integrity of the particular element in question. The skilled artisan will understand that a number of polymers may be used to form the pump housing element and the filtration cap element, including thermoplastics, some thermosets, and elastomers. Common thermoplastics include PMMA, cyclic olefin copolymer, ethylene vinyl acetate, polyacrylate, polyaryletherketone, polybutadiene, polycarbonate, polyester, polyetherimide, polysulfone, nylon, polyethylene, and polystyrene. Common thermosets include polyesters, polyurethanes, duroplast, epoxy resins, and polyimides. This list is not meant to be limiting. Functional filler materials such as talc and carbon fibers can be included for purposes of improving stiffness, working temperatures, and part shrinkage.

The pump housing element and the filtration cap element may be formed using a number of methods known to those of skill in the art, including but not limited to injection molding, blow molding, machining, etching, 3D printing, etc. In preferred embodiments, the test device base is injection molded, a process for forming thermoplastic and thermoset materials into molded products of intricate shapes, at high production rates and with good dimensional accuracy. The process typically involves the injection, under high pressure, of a metered quantity of heated and plasticized material into a relatively cool mold—in which the plastic material solidifies. Resin pellets are fed through a heated screw and barrel under high pressure. The liquefied material moves through a runner system and into the mold. The cavity of the mold determines the external shape of the product while the core shapes the interior. When the material enters the chilled cavities, it starts to re-plasticize and return to a solid state and the configuration of the finished part. The machine then ejects the finished parts or products.

In certain embodiments, the pump housing element comprises a light source positioned at a first location, and a light sensor positioned at a second location, and an optical path between the first and second locations such that, when no filtration cap element is in place, the light sensor is in optical communication with the light source. In various embodiments, the optical path is within the material forming the pump housing element (e.g., the plastic structure of the pump housing element transmits light in a manner akin to a light pipe. The optical path can extend through an aperture designed to receive a tang or other structure present on the filtration cap element such that when the filtration cap element is correctly installed on to the pump housing element, the tang or structure inserts through the aperture, thereby interrupting the path of light. In a preferred embodiment, the disruption of light is detected by the light sensor and serves as an indication that the filtration cap element is installed. This is not meant to be limiting. For example, correct installation of the filtration cap element may simply toggle a mechanical switch.

One or more light sources can also be configured to provide a visual indicator apparent on the pump housing element, the filtration cap element, or other structures making up a filtration device, in order to communicate various parameters to the user. Such parameters can include, but are not limited to, operational status of the vacuum pump (e.g., ready, on, off), charge status of a battery supply for the pump, remaining operational life of the filter element, vacuum level within the chamber, compliance with medical directives, etc. By way of example, a red visual indicator from a light source may indicate a filter that has reached the end of its useful life, and that the device is in need of a replacement of the filter cap element. Alternatively, a green visual indicator may indicate adequate charge of the battery supply which runs the pump. This is exemplary only, and is not meant to be limiting, and these data aspects may be performed by other elements of the device.

As noted herein, the filtration cap element supports a filtration membrane. A filtration membrane is a semi-permeable thin layer capable of separating contaminants as a function of their physical and or chemical properties. For example, the membrane can be designed to trap containments larger than the pore size of the membrane, removal through size exclusion, or as a function of a chemical property, for example, hydrophobicity or both. Preferred membranes provide enough mass transfer area to process the desired amount of flow corresponding to the desired vacuum level and time-to-operating-vacuum. The selected membrane provides high selectivity (rejection) properties for certain particles; resists fouling; and provides sufficient mechanical stability to withstand the desired force applied due to vacuum. It is preferred that the filtration membrane comprise a hydrophobic material so as to reduce the tendency of aqueous materials to enter and foul the pump. Suitable materials include films made of such hydrophobic polymers such as PTFE, track etched polycarbonate, polyethersulfone, etc. The filtration cap element is configured support a filtration membrane with a water breakthrough pressure of at least about 8 psi, more preferably at least about 15 psi, still more preferably at least about 20 psi, and still more preferably at least about 40 psi or more, coupled with a nominal pore size of about 20 µm or less, more preferably about 5 µm or less, and still more preferably about 0.25 µm or less, is preferred. The thickness of the filtration membrane is preferably between about 0.001 and about 0.02 inches. The term "about" as used herein with regard to any value refers to +/−10% of that value.

In certain embodiments, the vacuum pump filtration system may contain one or more sealable apertures. As used herein a sealable aperture is an opening through an element of the apparatus that can be closed or sealed from one side or the other with another element of the apparatus creating an air-tight or water tight seal. In a preferred embodiment a seal is created via surfaces designed to receive an O-ring. As used herein an O-ring is a packing or gasket in the form of a ring made of a pliable material designed to be seated in a groove and compressed during assembly between two or more vacuum pump filtration system elements creating a seal at the interface. In a preferred embodiment the pump housing assembly may contain one or more recesses that create an O-ring mating surface such that when the control module is mounted to the pump housing assembly an air-tight seal is established. This permits communication between the low vacuum side and the atmospheric pressure side of the filtration system without a loss of vacuum.

In certain embodiments, the pump housing element may contain one or more apertures into which check valve(s) are placed. As used herein a check valve is a directional, one-way valve that allows liquid or gas to flow in only one direction. In a preferred embodiment the check valve is mounted to the pump via the aperture on the pump housing element and are oriented such that the valve opens when the pump is energized and drawing air, and closes when an operating level of vacuum is reached and the pump is turned off.

In certain embodiments, the filtration cap element is configured to withstand a desired pressure differential without failure of the filtration membrane to maintain the pressure differential. As used herein, a differential pressure is defined as the net change in pressure from one side of a filter to the other. Exceeding a pressure differential can cause rupture of a membrane and failure of the filtration element. In a preferred embodiment the filtration cap element is configured such that the filtration membrane is able to withstand a pressure differential of about 0 to about 5 centimeters of water and up to about 25 cm of water.

In certain embodiments, the filtration cap element is configured to withstand a desired flow rate of air through the filtration membrane without failure of the filtration membrane. As used herein, flow rate is a measure of the amount of material that flows through a filter at a defined pressure. Water flow rate is the amount of water that flows through a filter at a defined rate. Air flow rate is the amount of air that flows thought the filter. Flow rates are related to the degree of contamination, differential pressure, total porosity and filter area. Air flow rate is generally expressed in liters/minute at a given pressure. In a preferred embodiment the filtration cap element is configured such that the filtration membrane is able to withstand flow rates of up to about 3 liters per minute.

The filtration cap element may provide a filtration membrane mating surface which mates with the filtration membrane for support of the filtration membrane. An adhesive, such as a structural or pressure-sensitive adhesive, may be provided on a surface of the filtration membrane, the mating surface, or both, to retain the filtration membrane in a desired location within the filtration cap element and maintain an airtight seal around the filter membrane. Typical biologically compatible pressure-sensitive adhesive formulations are acrylics, rubbers and silicones, optionally blended with tackifiers, antioxidants, pigments, and fillers. Acrylic-based pressure-sensitive adhesives are made from higher alkyl esters of acrylic acid without need of tackifiers and provide excellent physical properties. See, e.g., Zbigniew Czech and Agnieszka Kowalczyk (2011). Pressure-Sensitive Adhesives for Medical Applications, Wide Spectra of Quality Control, Dr. Isin Akyar (Ed.), ISBN: 978-953-307-683-6, InTech, DOI: 10.5772/23827. In an embodiment of the invention the area of adhesion is of a similar yet smaller size and shape as the filtration membrane thereby providing an overlapping region to affix the membrane to the filtration cap element.

The filtration cap element can also provide a supporting structure for the filtration membrane in the form of a mesh or other perforated structure extending to span the filtration cap element membrane opening that the filtration membrane covers. The supporting structure can entail parallel beams, intersecting beams or apertures. As used herein a beam is defined as a traverse structural piece or pieces that add support to the filtration cap element features. In an embodiment the supporting structure is a series of parallel beams located on the same plane as the filtration membrane mating surface. In a further embodiment the supporting structure contains a second series of parallel beams on the interior surface of the filtration cap element oriented in a divergent manner from the beams located on the exterior of the cap. In a preferred embodiment the interior beams are directionally arranged to guide the flow of air to the intake of the pump.

The filtration cap element preferably mates to the pump housing element in a manner that frictionally secures one to the other and prevents air from escaping from the mated surfaces. In a preferred embodiment, the gap between the pump housing mating surface, the intake port of the vacuum pump and the interior surface of the filtration cap element is between 3 and 5 thousandths of an inch.

The filtration cap element, the pump housing element, or both, may also be constructed to provide one or more access points for optional elements to be included with the device. By way of example, one or more apertures may be provided to receive sensors within the pump housing element. Such sensors may be configured to monitor of the interior of the vacuum chamber for vacuum level, temperature, etc. Such sensors may be in communication with a processor element which may be part of the pump housing element. The electronics within the pump housing element preferably include a battery or other power supply which powers both the vacuum pump and any sensors or other electronics. Numerous battery technologies are known in the art, including common alkaline batteries, oxide batteries, lithium batteries, etc. There are three preferred battery technologies that could be employed: Nickel Cadmium (NiCad), Nickel Metal Hydride (NiMH) and Lithium Ion (Li-ion), and most preferred are Li-ion batteries.

Those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Figure 13:
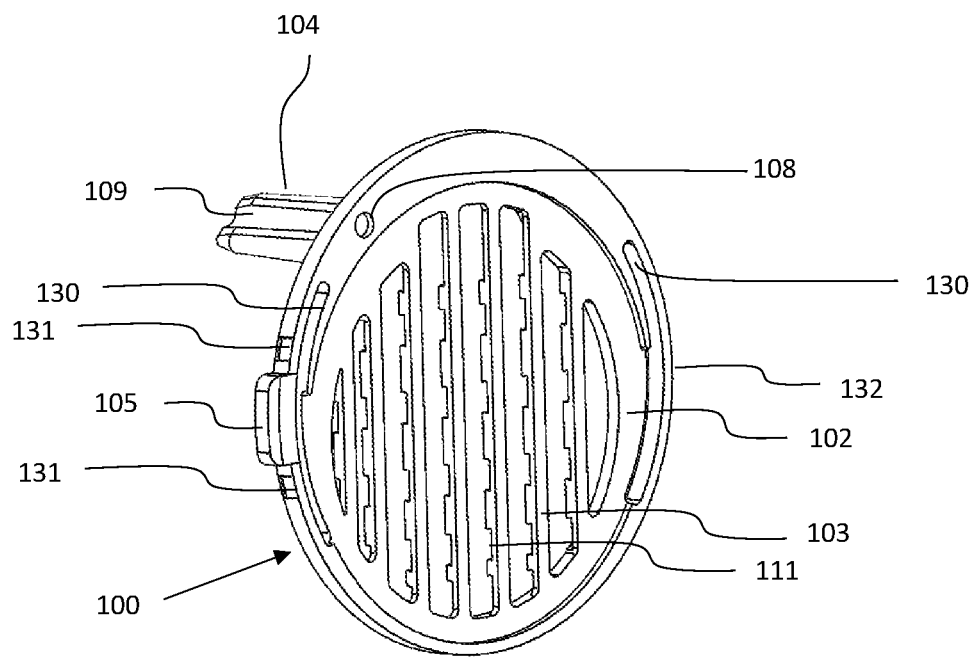

FIG. 13 is an angled exterior surface view of an illustrative embodiment of the filtration cap 100 without the filtration membrane installed showing the filtration cap removal tab 105, the membrane mounting surface 102, including the membrane support structure 103 and underlying supporting air channels 111, aperture 108 for interior sensors, a compliance feature 104 with sensor channel 109 extending from the interior surface of the filtration cap, filter cap frame flex features 130 and filtration cap affixing tab(s) 131/132.

Figure 14:
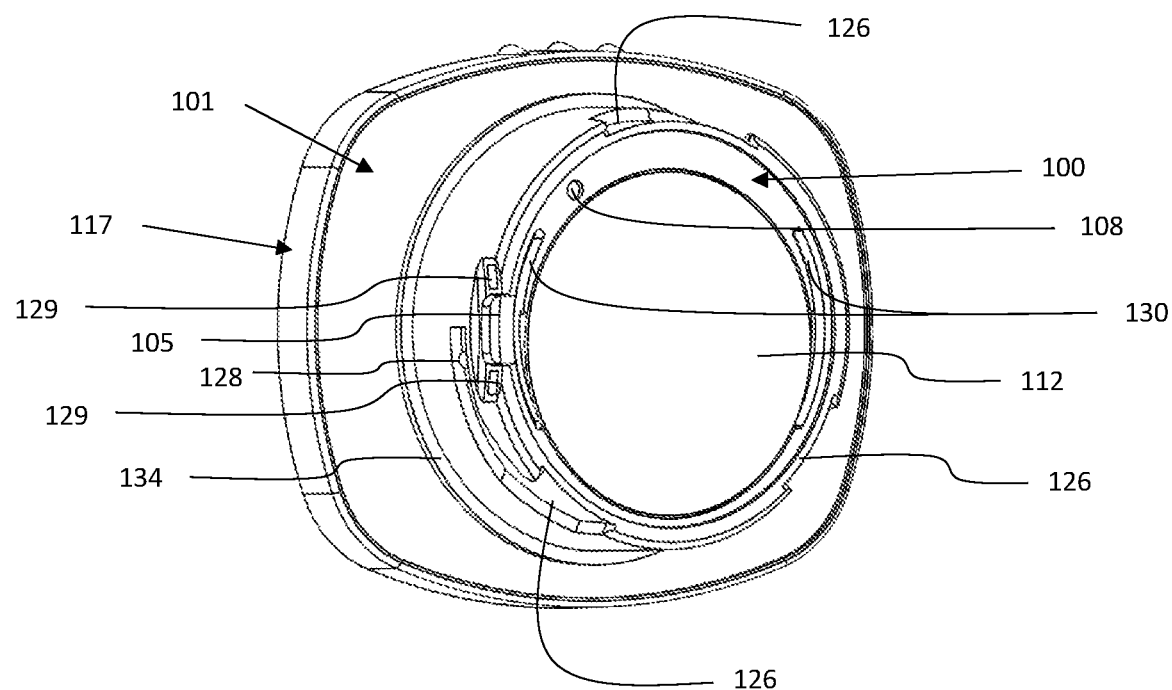

FIG. 14 is an illustrative embodiment of the assembled vacuum pump apparatus including the filtration cap element 100, vacuum pump housing 101, vacuum pump exhaust cap 117, including removal tab 105, filtration membrane 112, an aperture 108 for interior sensors, filter cap frame flex features 130 and filtration cap affixing tangs 131/132, including bayonet recess(s) 126 and vacuum chamber sealing/O-ring surface 134.

Figure 15:
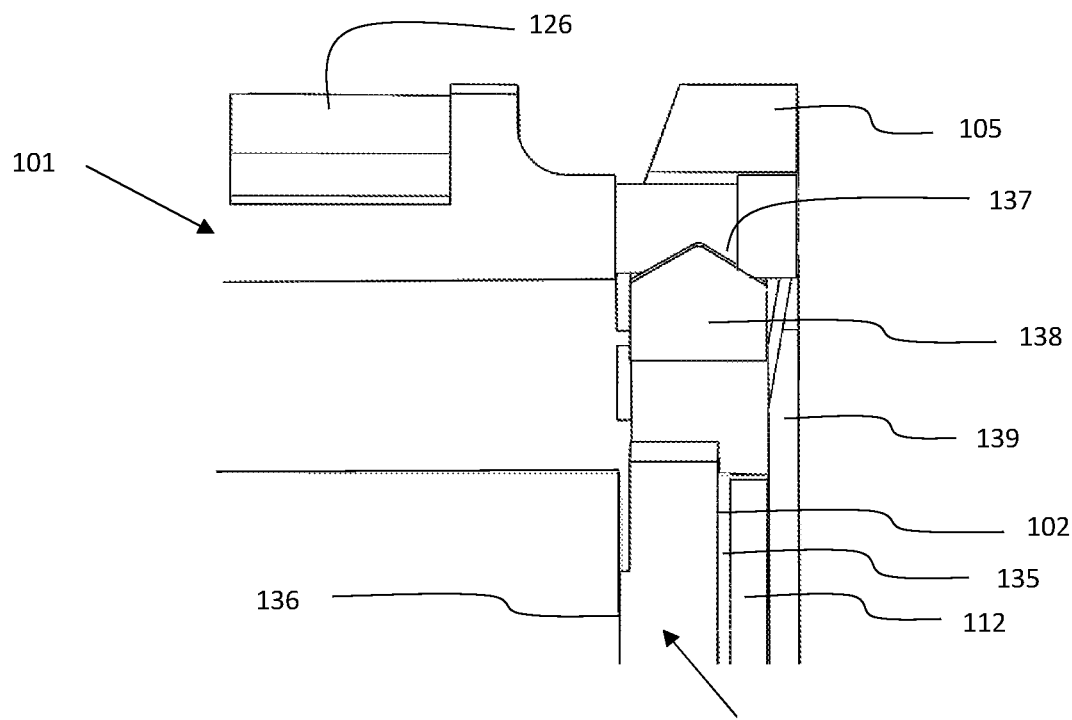

FIG. 15 is an illustrative embodiment of cross section of the assembled vacuum pump apparatus including the filtration cap element 100, vacuum pump housing 101, filtration cap removal tab 105, filtration membrane 112, bayonet recess 126, pump housing tapered recess/aperture 137, filtration cap tapered affixing tab 138, pump housing interior rim 139, filtration membrane mounting surface 102, adhesive layer 135, and vacuum pump intake surface 136.

DETAILED DESCRIPTION OF THE INVENTION

The present invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the present invention. The examples used herein are intended merely to facilitate an understanding of ways in which the invention may be practiced and to further enable those of skill in the art to practice the invention. Accordingly, the examples should not be construed as limiting the scope of the invention. In the drawings, like reference numerals designate corresponding parts throughout the several views.

In the present invention a pump housing is designed to secure to an evacuation chamber and to accommodate associated components and circuitry including, but not limited to, a vacuum pump, printed circuit board(s) (PCB), microprocessors for controlling, sensors, switching mechanisms, wireless interfaces, radio frequency identifying features, acoustic sources, acoustic sensors, electronic charging features, light features, for example light emitting diode (LED) visual indicators and other light sources, and a filtration cap that mates with the pump housing that includes a filtration membrane, filter membrane support structure, an aperture(s) for sensor port(s), a compliance tang/feature that extends in to the pump housing and is guided by clocking features molded into the pump housing, ensuring proper alignment of the filtration cap.

Figure 1:
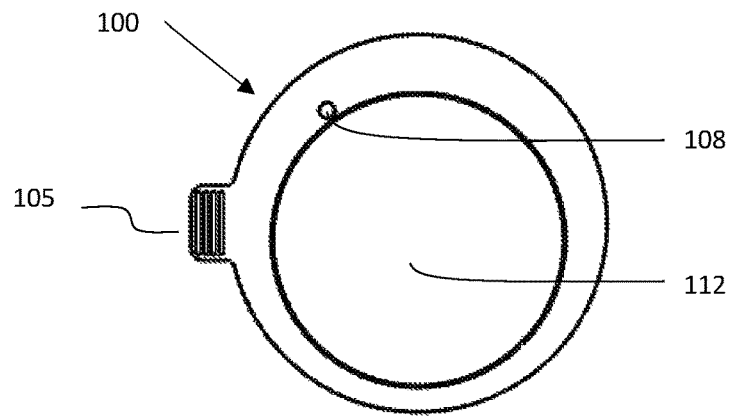
FIG. 1 is an exterior surface view of an illustrative embodiment of the filtration cap element 100, with the filtration membrane 112 in place over the membrane supporting feature 103, also shown is a removal tab 105 and an aperture 108 to allow interior sensors to assess conditions beyond the filter membrane.
Figure 2:
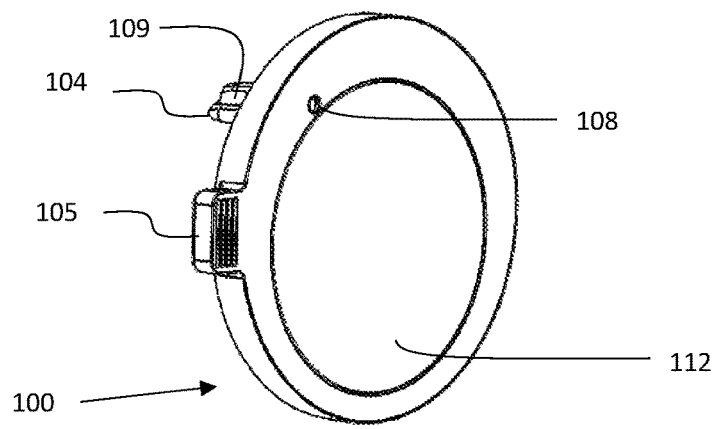
FIG. 2 is an angled exterior surface view of an illustrative embodiment of the filtration cap 100 with the filtration membrane 112 in place over the membrane supporting feature, a textured removal tab 105, an aperture 108 for interior sensors and a compliance feature 104 with sensor channel 109 extending from the interior surface of the filtration cap.
Figure 3:
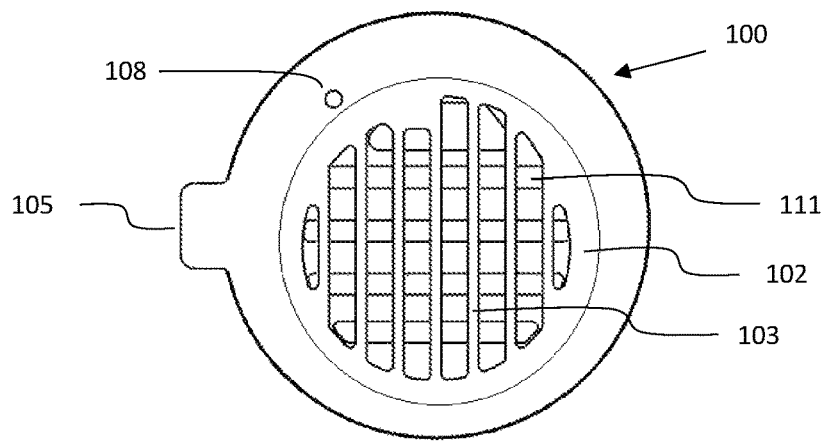
FIG. 3 is an exterior view of an illustrative embodiment of the filtration cap element 100 without the filtration membrane installed showing the filtration cap element removal tap 105, the membrane mounting surface 102 including the membrane support structure 103 and underlying supporting air channels 111 and aperture for interior sensors 108.
Figure 4:
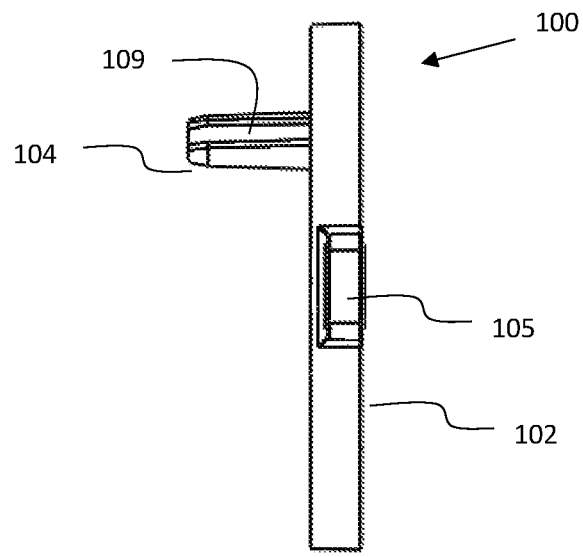
FIG. 4 is a side view of an illustrative embodiment of the filtration cap element 100 including the filtration membrane mounting surface 102, a filtration cap element removal tab 105 and compliance tang 104 that extends from the interior surface of the cap and includes a trough 109 that is aligned with the sensor port aperture 108 and when installed, the guidance tangs of the vacuum pump housing element.
Figure 5:
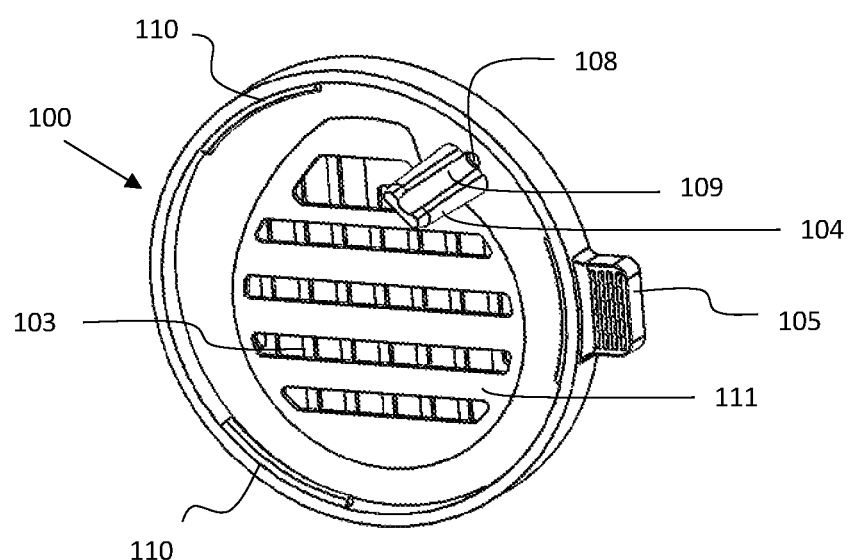
FIG. 5 is an interior surface view of an illustrative embodiment of the filtration cap element 100 including the underside of the membrane support structure 103, supporting air channels 111, the compliance tang 104 containing the aperture for interior sensors 108 through the filtration cap element 100 and trough 109 and tangs along the interior edge 110 of the filtration cap element for fixing the cap element to the housing element 101 and removal tab 105.
Figure 6:
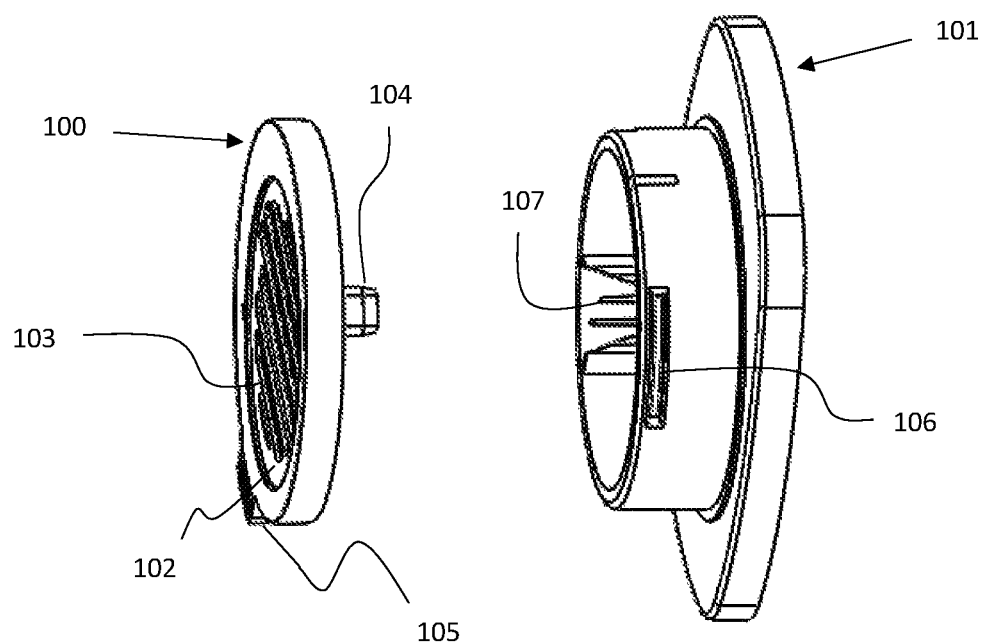
FIG. 6 is an interior surface view of an illustrative embodiment of the filtration cap element 100 including the central membrane support feature 103, membrane mounting surface 102, the compliance tang 104, filtration cap element removal tab 105, and vacuum pump housing element 101 including compliance tang guide features 107 and recess 106 along the exterior of the vacuum pump housing element to receive tangs from filtration cap that affix the filtration cap element 100 to the vacuum pump housing element 101.
Figure 7:
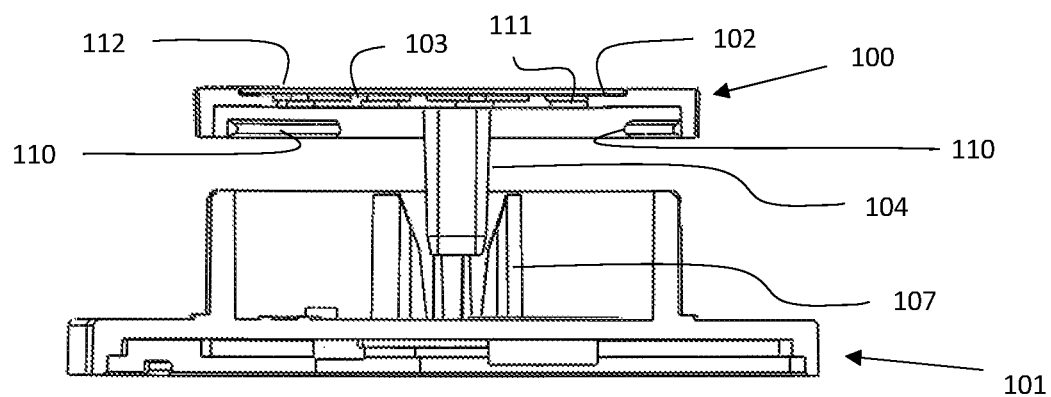
FIG. 7 is a cross sectional side view of an illustrative embodiment of the filtration cap element 100 including the filtration cap element compliance tang 104, filtration cap element securing tang(s) 110 along the interior rim of the cap for fixing the filtration cap element 100 to the vacuum pump housing element 101, filtration membrane 112, filtration membrane mounting surface 102, filtration membrane support structure 103, supporting air channels 111, and vacuum pump housing element 101 including compliance tang(s) guide features 107.
Figure 8:
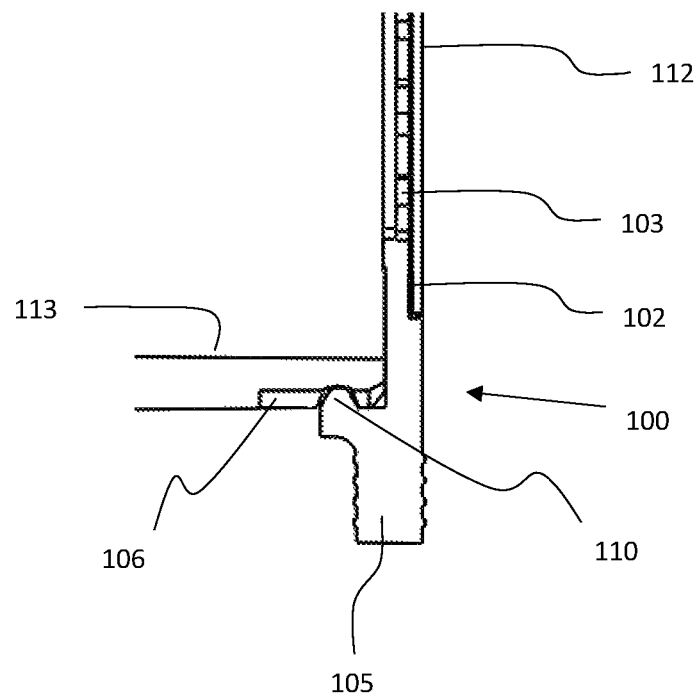
FIG. 8 is a cross sectional view of an illustrative embodiment of the filtration cap element 100 mounted to the vacuum pump housing element including 101 the filtration cap element removal tab 105, filtration cap element affixing tang(s) 110 along the interior of the cap, filtration membrane 112, membrane support structure 102, supporting air channels 103, and vacuum pump housing wall 113 including a filtration cap element tang receiving recess 106.
Figure 9:
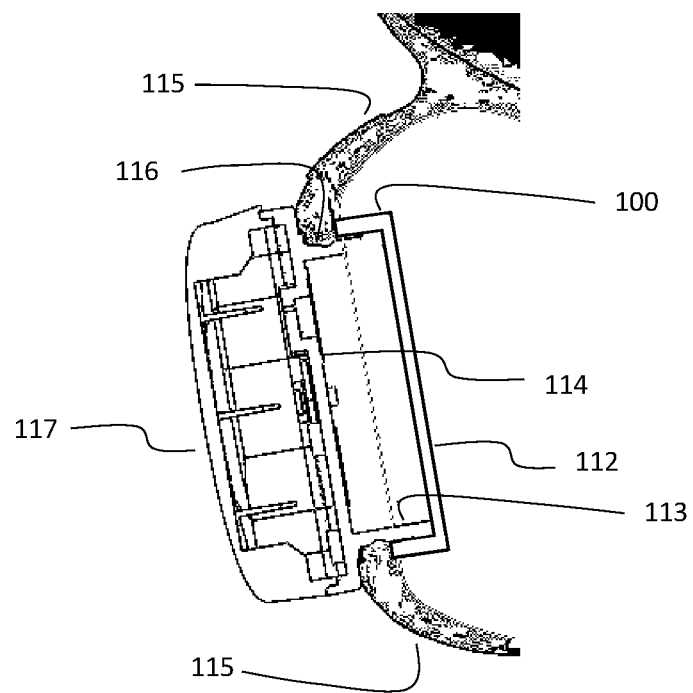
FIG. 9 is a cross sectional view of an illustrative embodiment of the vacuum pump apparatus with the vacuum pump housing element 101 inserted through a vacuum chamber aperture 116 of a vacuum chamber element 115 and mounted via the filtration cap element 100 affixed from the inside of the vacuum chamber element 115, also shown is the vacuum pump mounting surface 114, filtration membrane 112, and vacuum pump assembly exhaust cap 117.

In an embodiment of the present invention the vacuum pump housing element 101 is installed through the exterior of an evacuation chamber 115 through vacuum pump aperture 116 and affixed via installation of the filtration cap element 100. FIG. 9. The benefit of the filter cap arrangement is to provide optimal performance of the vacuum pump to meet user expectations. Loss of vacuum or poor vacuum performance will result in the chamber dislodging from the user or not achieving therapeutic levels.

The vacuum pump housing element 101 may be held in place within the vacuum pump aperture 116 of the evacuation chamber 115 in a number of manners. For example, the filtration cap element 100 may be mated to the vacuum pump housing element 101 through the aperture 116 such that the edge of the vacuum pump aperture 116 is sandwiched between the filtration cap element and the vacuum pump housing element, thereby forming a sealed structure as shown in FIG. 9. Proper mating of the filtration cap 100 to the vacuum pump housing 101 ensures the entire vacuum assembly is tightly secured to the vacuum chamber 115 in addition to ensuring correct clearance between the interior surface of the filtration cap and the intake of the vacuum pump.

Alternatively, the filtration cap element 100 may be mated to the vacuum pump housing element 101 separately from the evacuation chamber 115 and then inserted into the vacuum pump aperture 116 in a manner which forms a sealed structure. In this embodiment, a sealing/o-ring surface 134 including an o-ring or other compliant member may be present either on the assembled vacuum pump element and/or within the vacuum pump aperture to provide a sufficiently leak-free seal to the evacuation chamber.

In certain embodiments, a releasable bayonet-type fastening system may be used to releasably attach such an assembled vacuum pump element to evacuation chamber 115. In an example of such a bayonet mount, a cylindrical male fitting (i.e., the assembled vacuum pump element) is configured to insert into a female receiving element (i.e., vacuum pump aperture 116), and the elements are rotated relative to one another in order to achieve fastening. The male (or female) fitting may contain one or more radial pins or tangs, and the female (or male) element may contain one or more corresponding slots or recesses 126 configured to receive the pins or tangs. These recesses may be shaped, for example, like a letter "L" that contains a short upward segment at the end of the horizontal arm wherein the tang of the male feature slides into the vertical arm of the "L" and, upon rotation across the horizontal arm of the "L", the tang aligns with the upward segment. A spring mechanism can be used to assist in securing the two features together. A bayonet mount may further contain a stopping feature 128 wherein rotation of a feature is prevented past a designated point. A stop feature may be present to align and orient the pieces in to a preferable configuration, to prevent over-rotation or both. Bayonet features may also be configured in an asymmetric fashion in order to further guide proper alignment, assembly and singular orientation.

In particular, the evacuation chamber described herein relates but is not limited to an external therapy appliance for relieving upper airway obstruction. U.S. patent application Ser. Nos. 12/002,515, 12/993,311 and 13/881,836 which are hereby incorporated by reference in their entirety including all tables, figures and claims, describes a therapy appliance for relieving airway obstruction. As described therein, a device is configured to fit under the chin of a user at an external location corresponding to the soft tissues overlying the upper respiratory passages of the neck.

The therapy appliance of the present invention comprises a structural member that provides a chamber between an inner surface of the appliance and the skin of the throat, where the structure is sufficiently rigid to withstand the required partial vacuum created within the space, and a peripheral rim that seals to the skin of the user in order to enclose the space. The vessel may be formed, molded, or fabricated from any material or combination of materials. Non-limiting examples of such materials suitable for constructing the therapy appliance include plastics, metals, natural fabrics, synthetic fabrics, and the like. The appliance may also be constructed from a material having resilient memory such as silicone, rubber, or urethane.

The chamber of the present invention further comprises an aperture through which a vacuum pump assembly is affixed. The term "vacuum pump" as used herein refers to a device that removes gas molecules from a sealed chamber in order to leave behind a partial vacuum. In an embodiment of the invention a vacuum is created using a piezoelectric disc pump however other configurations will be readily apparent to those skilled in the art.

Structural embodiments of the apparatus may vary based on the size of the device and the description provided herein is a guide to the functional aspects and means. Additionally, the pump housing element 101 and filtration cap element 100 may be provided in an annular or oblong shape.

The pump housing element is designed with raised guiding surfaces 107 along an interior wall that accommodates a filtration cap element 100 with a corresponding compliance tang 104. The compliance tang extends from the interior surface of the cap in to the pump housing with the clocking surface allowing for a singular orientation when installing the filtration cap element 100. Additionally, the compliance tang 104 is designed to toggle a switch located within the pump housing at an optimal depth. The switch mechanism can be mechanical, electronic or optical. Only when the filtration cap element 100 is installed in the correct orientation and at the correct sealing depth would the compliance tang 104 activate circuitry and allow the pump to function. This ensures that the pump would only cycle with the filtration cap element 100 correctly installed.

In the present invention the pump is designed to be inoperable without the filtration cap element 100 in place. User compliance is obtained by a switching circuit that is triggered upon the proper installation of the filtration apparatus. Proper installation is defined by proper alignment and proper installation depth of the filtration cap element 100. Any switching mechanisms may be used including mechanical, electrical or optical or any combination of available mechanisms.

In an embodiment of the invention the installation of the correct cap is ensured through automated tracking using electronic circuits. These radio frequency identification circuits (RFID) are capable of sending and receiving radio signals identifying and differentiating one product from another. In the present invention, in order to ensure installation of an appropriate filtration cap to the vacuum pump housing, the filtration cap is supplied with a RFID tag that can be affixed or molded thereto and the associated RFID sensor is integrated into the pump assembly circuitry. Only when the correct cap is installed will the vacuum pump activate.

High frequency piezoelectric disc pumps suffer leakage when the pump is cycled off. In an embodiment of the invention the vacuum pump is fitted to a check valve 121. Check valves are one-way directional valves that prevent reversal of air flow. The pump housing is designed with a vacuum pump mounting surface that contains apertures for the placement of a check valve 121. When the vacuum pump cycles off backflow forces the valve closed avoiding loss of vacuum in the evacuation chamber. By avoiding vacuum loss through the pump, cycle times are minimized extending pump as well as battery life.

The compliance tang 104 is located distally within the filtration cap element 100 and adjacent to the removal tab 105 to minimize distortion upon removal of the cap from the housing. The compliance tang 104 is shaped with a trough 109, shoulders and a narrowing end that assist in providing not only a switching means but also structural integrity with the trough providing a sealed channel from the aperture in the cap to the interior sensor(s) in the vacuum pump housing element.

Figure 10:
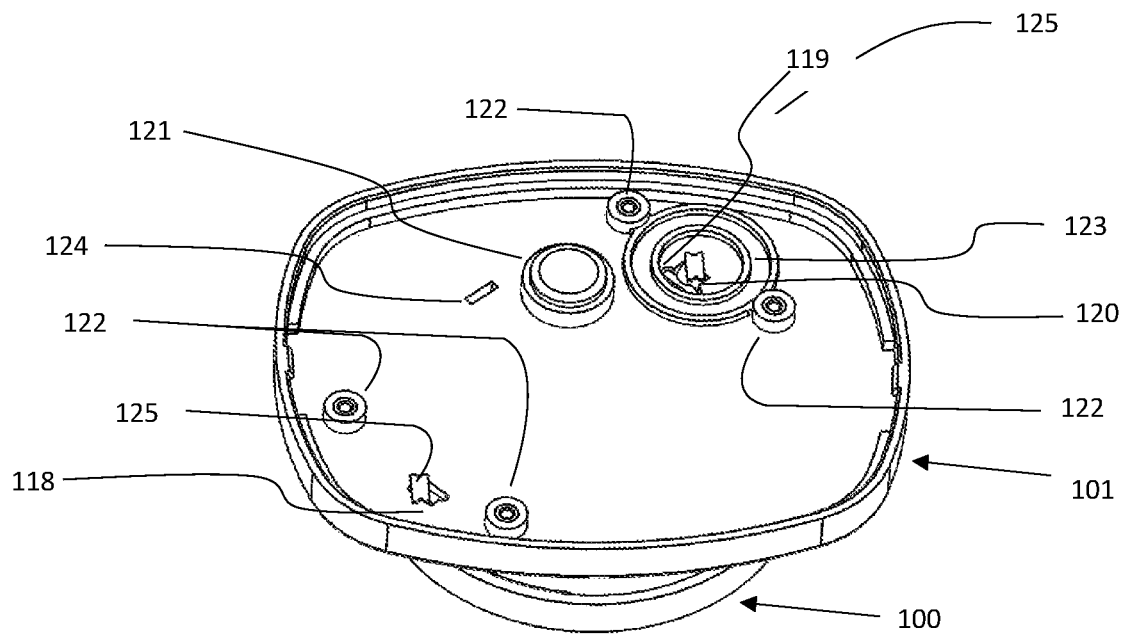
FIG. 10 is an exterior view of an illustrative embodiment of the vacuum pump housing element 101 including light source recess 118, optical sensor/switch recess 120, light reflectors 125, O-ring trough 123, compliance tang aperture 119, check valve mounting surface 121, control module mounting surfaces 122, vacuum pump housing aperture for a flexible circuit board 124 and filtration cap element 100.
Figure 11:
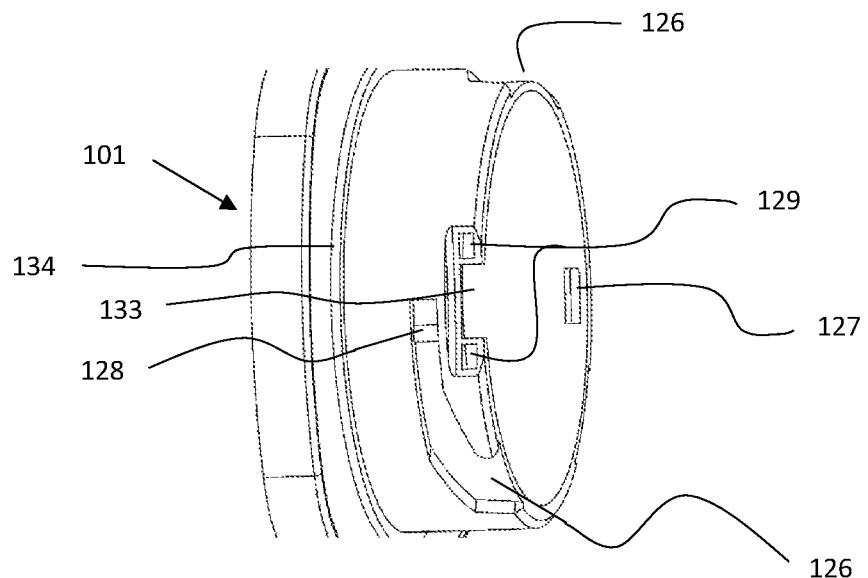
FIG. 11 is a view of an illustrative embodiment of the vacuum pump housing 101 including bayonet recess(s) 126, filter cap affixing tab aperture (opposite filter cap removal tab) 127, filter cap affixing tab apertures adjacent filter cap removal tab 129, filter cap removal tab recess 133, bayonet stop 128, and vacuum chamber sealing/O-ring surface 134
Figure 12:
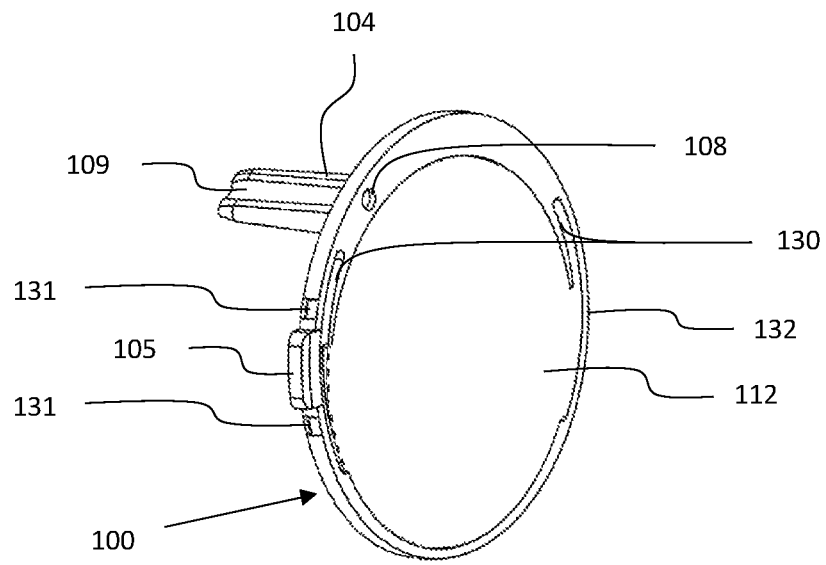
FIG. 12 is an angled exterior surface view of an illustrative embodiment of the filtration cap 100 with the filtration membrane 112 in place over the membrane supporting feature, a removal tab 105, an aperture 108 for interior sensors, a compliance feature 104 with sensor channel 109 extending from the interior surface of the filtration cap, filter cap frame flex features 130 and filtration cap affixing tabs 131.

The vacuum pump housing element contains apertures, recesses and mounting points to accept many of the features included in the device. The housing exterior FIG. 10 contains mounting points 122 for a circuit board and circuit board O-ring trough 123 that is flanked by two of the PCB mounting points 122. When the PCB is installed, the mounting points 122 secure an air tight seal between the housing and the sensors located within the inner area of the O-ring on the PCB.

The vacuum pump housing element contains an aperture 124 for the insertion of a flexible printed circuit board (flexi) that connects the vacuum pump on the interior of the housing to the controlling circuitry on the exterior of the housing.

The pump housing element 101 further contains a recess for a light source 118 and a switching mechanism 120. Upon mounting of the PCB to the vacuum pump housing the light source, light sensor and or switch locate within these recesses. The pump housing element further contains a compliance tang aperture 119. When the filtration cap element is installed the compliance tang inserts through the aperture to toggle a switching feature on the PCB.

In an embodiment of the invention the light source can be a light emitting diode (LED). A feature of the LED is to provide a user interface element by allowing the user to view the LED state through the housing body. This can be used to indicate additional product functions or modes in addition to performing filter presences tests.

In a preferred embodiment of the invention the switch mechanism would include an optical switch. Detection of the filtration cap element 100 is achieved by having a vacuum pump housing element 101 made of an optical grade, translucent or transparent, material, a light source, a light sensor and a light interrupter. A beam of light emitted from an on-board LED is focused on an electronic receptor located along the path of the compliance tang of the filtration cap. The receptor is coupled to a switching mechanism that only activates the pump circuitry when the beam of light is interrupted. Upon correct installation of the filtration cap 100 the compliance tang 104 would interrupt the beam of light indicating compliance and allowing activation of the pump function. The switching mechanism may be coupled to a second LED of a different color or location to indicate pump readiness.

The surface of the housing body that the light travels through is parallel to the PCB system, however the LED and the sensor are mounted perpendicular to the PCB surface. In order to guide the light beam from the LED to the sensor, molded into the housing are light reflectors 125 angled at 45 degrees along the light path. When the LED is illuminated, the light bounces off the 45 degree face, travels through the housing body 101, through the compliance tang aperture 119 and finally enters the light sensor aperture 120. If the filtration cap element 100 is installed correctly and the compliance tang 104 is present the light will not reach the sensor.

To accommodate for varying ambient light conditions it is necessary to take two measurements from the light sensor to determine if the filtration cap element is present. First a reading is taken with the LED turned off. This value is the 'normal'. Then the LED is turned on and the sensor is read again. This is 'test'. If the value of 'test' roughly equals the value of "normal" the filter is present. Conversely, if 'test' is greater than 'normal' the filter is determined not present and the vacuum pump will not cycle on.

The filtration cap element 100 and pump housing element 101 are designed to cooperate. In an embodiment of the invention the filtration cap 100 may be secured to the vacuum pump housing 101 via a tab(s) 110 located on the interior rim of the cap. The pump housing 101 may contain a recess(s) 106 around its outer surface to receive the tab(s) 110 of the filtration cap 100. The tab(s) 110 are designed to mate with recessed receiving surfaces on the exterior the pump housing and snap in place. In an embodiment of the invention the tabs are designed with an angular contact surface creating a natural rate, tightly securing the filtration cap to the pump housing and flush with the vacuum pump intake.

In an alternative embodiment where the filtration cap element 100 and the pump housing element 101 are designed to cooperate, the filtration cap element 100 may be secured to the pump housing element 101 via recesses or apertures 127 and 129 on the inside rim/through the inside rim 139 of the vacuum pump hosing element 101 with tab(s) 131/132 located on the exterior edges of the filtration cap element 100 FIG. 14. The tab(s) 131/132 are designed to mate with the recessed or aperture receiving surfaces on the interior rim 139 of the pump housing and snap in place. The filtration cap element 100 may also contain flexible features in the form of a tapered apertures 130 in order to allow movement of portions of the filtration cap element to create a rate at the cap perimeter, tightly securing the filtration cap element 100 when installed to the pump housing element 101 and flush with the vacuum pump intake.

In a further embodiment where the filtration cap element 100 and the pump housing element 101 are designed to cooperate, the filtration cap element 100 may be secured to the pump hosing element 101 via tapered recess/apertures 137 on the inside rim/through the inside rim 139 of the vacuum pump housing element 101 with tapered tab(s) 138 located on the outside edge of the filtration cap element 101, FIG. 15. The tabs are designed to mate with the receiving surface(s) and snap in to place. The taper creates a bias toward the interior of the pump housing forcing the filtration cap element 100 inward and on to the surface of the vacuum pump 136.

The filtration cap element 100 contains a removal tab 105 located on the outer perimeter of the cap, near the compliance tang 104 and, in some examples, center to one of the interior tangs 110. When the removal tab 105 is pulled outward a bending moment releases the first interior tang 110. When the first interior tang 110 is released a mechanical advantage is achieved moving radially outward releasing the remaining tangs and releasing the filtration cap element 100.

The filtration cap element 100 can be made of any compatible and pliable material. In an embodiment of the invention the filtration cap element 100 is produced of a semi rigid polymer that allows the cap to be removed directionally via a removal tab 105. The semi rigid polymer also determines the rate of the securing tangs 110 and ultimately sealing pressure of the filtration cap 100 to the vacuum pump housing 101.

An additional feature of the filtration cap element 100 is the placement of a filter 112. In a preferred embodiment the filter is selected from a group of hydrophobic filters. The filter is secured to the filtration cap using a pressure sensitive adhesive (PSA) FIG. 15, 135. The membrane can be made of any hydrophobic material with ranges in pore size from 0.25 um to 20 um, and in a preferred embodiment a pore size range of 0.25 um to 5 um. The filtration membrane is further defined as being able to withstand a pressure differential of 0 to 5 centimeters of water at a flow rate of up to 3 liters per minute. In addition to being designed to withstand a pressure differential, more importantly the filtration apparatus must not cause excessive differential pressure from the exterior of the filter to the pump intake. Large variations in pressure diminish pneumatic performance and ultimately battery life.

The filter membrane 112 is affixed and supported on the filtration cap using a mounting surface 102 and support channels 103. The mounting surface mimics the membrane shape with enough overlap to provide an appropriate surface for the edge of the membrane to adhere to using the PSA FIG. 15, 135. The filtration membrane is further supported via a series of channels molded into the filtration cap that extend across the remaining opening of the filter mounting space.

The filtration membrane 112 support structure consists of layers of intersecting channels that are molded into the filtration cap. The first layer of channels 103 is located on the exterior side of the filtration cap and on the same plane as the membrane mounting surface 102. This provides for additional support via a direct contact surface between the filter membrane and the filter cap channels. The contact area of the support structure layer minimizes the likelihood that the membrane will rupture when vacuum is applied. The second layer of channels 111 is located behind the first and in an intersecting pattern. The pattern of the entire support feature is designed to channel air toward the intake port of the vacuum pump. The size of the channels may vary in size based on the size of the filtration cap and membrane pore size but optimized to not significantly increase the resistance to airflow across and through the filter. An additional benefit of the support feature is that it can act as a visual indicator of contamination. Areas upon which the membrane does not directly contact a support structure channel would visibly discolor as a result of gross contamination from particulate matter trying to pass through the unblocked areas of the filter.

An additional feature of the pump filtration device is the placement of an pump housing exterior cap 117 located on the surface of pump housing 101 external to the vacuum chamber 115 and opposite the filtration cap element 100. The pump housing exterior cap 117 may serve as a means to seal components mounted on the exterior of the pump housing as well as contain apertures serving as pump exhaust features. The cap may be made of any compatible material both solid and or translucent in color and generally rigid. In an embodiment of the invention an exterior cap 117 that is translucent either in whole or part may allow a user to observe device status via visual indicators located within the device.

In an embodiment of the invention, the pump housing exterior cap 117 may be releasably adhered via structural means for example with tabs and recesses or bayonet fittings or be more permanently affixed by gluing or welding. In a further embodiment of, the pump housing exterior can be made of a semi-rigid polymer that allows the cap to be installed and removed over the vacuum pump housing. The semi rigid polymer also determines the rate of any securing features and in instances of the exterior cap being removable can hold the cap in place during use or in instances of the exterior cap being permanently affixed hold the cap in place during assembly and gluing or welding.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A vacuum pump filtration system comprising:
a pump housing element comprising a vacuum pump;
a filtration cap element comprising a filter membrane;
an evacuation enclosure configured to mate with a portion of the human body and thereby create a chamber having an interior volume formed between the human body and the evacuation enclosure, the evacuation enclosure comprising an aperture to receive the pump housing element,
wherein
the filtration cap element comprises a mating surface configured to releasably engage with a receiving surface on the pump housing element to form an integral pump/filter unit,
a wall portion of the pump housing element inserts through the aperture to position the receiving surface within the interior of the evacuation enclosure, and the mating surface of the filtration cap engages the receiving surface from within the interior of the evacuation enclosure such that an edge portion of the evacuation enclosure forming the aperture is entrapped between the pump housing element and the filtration cap element, thereby forming a substantially airtight seal of the aperture upon formation of the integral pump/filter unit, and
upon sealing of the aperture by the integral pump/filter unit, the filter membrane is positioned such that air being removed by the vacuum pump from the interior volume within the chamber must pass through the filter membrane prior to reaching the vacuum pump.

2. A vacuum pump filtration system according to claim 1, wherein the filtration cap element is configured as a disposable unit and the pump housing element is configured as a reusable unit in normal use.

3. A vacuum pump filtration system according to claim 1, wherein the filtration cap element, the pump housing element or both comprise one or more structural elements configured to ensure compatibility of the filtration cap element and the pump housing element and/or proper orientation of the filtration cap element relative to the pump housing element.

4. A vacuum pump filtration system according to claim 3, wherein the one or more structural elements comprise one or more tangs on the filtration cap element which insert into corresponding acceptance location(s) on the pump housing element in a predetermined configuration selected to prevent incompatible filtration cap elements from engaging with the pump housing element.

5. A vacuum pump filtration system according to claim 4, wherein the one or more structural elements comprise one or more tangs on the pump housing element which insert into corresponding acceptance location(s) on the filtration cap element in a predetermined configuration selected to prevent incompatible filtration cap elements from engaging with the pump housing element.

6. A vacuum pump filtration system according to claim 1, wherein the pump housing element comprises a control module configured to control vacuum pump on/off cycles and/or vacuum pump operating speed, and a battery for powering the control module and vacuum pump.

7. A vacuum pump filtration system according to claim 6, wherein the pump housing element comprises a light source positioned at a first location, and a light sensor positioned at a second location, and an optical path between the first and second locations such that, when no filtration cap element is in place, the light sensor is in optical communication with the light source, and wherein when the filtration cap element correctly engages the pump housing element, the optical communication is interrupted, and wherein the light sensor is in communication with the control module to prevent operation of the vacuum pump when the filtration cap element is not correctly engaged with the pump housing element.

8. A vacuum pump filtration system according to claim 6, wherein the pump housing element comprises a mechanical switch configured such that, when no filtration cap element is in place, the mechanical switch is in a first position, when the filtration cap element correctly engages the pump housing element, the mechanical switch is in a second configuration, and wherein the mechanical switch is in communication with the control module to prevent operation of the vacuum pump when the filtration cap element is not correctly engaged with the pump housing element.

9. A vacuum pump filtration system according to claim 6, wherein the pump housing element comprises an electronic tag reader configured to read a corresponding electronic tag on the filtration cap to determine compatibility between the filtration cap element and the pump housing element.

10. A vacuum pump filtration system according to claim 6, wherein the pump housing element comprises one or more environmental sensors configured to communicate with the control module.

11. A vacuum pump filtration system according to claim 10, wherein the one or more environmental sensors communicates data corresponding to the vacuum level within the interior volume within the chamber to the control module.

12. A vacuum pump filtration system according to claim 6, wherein the control module monitors useful lifetime of the filtration cap element as a function of operation of the vacuum pump, and provides a user notification of a filtration cap element that has reached the end of its useful lifetime.

13. A vacuum pump filtration system according to claim 12, wherein the control module prevents operation of the vacuum pump if the filtration cap element has reached the end of its useful lifetime until the filtration cap element is replaced.

14. The vacuum pump filtration system according to claim 1, wherein the pump housing element comprises one or more check valves configured such that the check valve(s) opens when the pump is energized and drawing air, and closes when an operating level of vacuum is reached and the pump is turned off.

15. The vacuum pump filtration system according to claim 1, comprising a filtration mating surface and mechanical support to the filtration membrane such that the filtration membrane withstands a pressure differential of 0 to 5 centimeters of water without failure of the filtration membrane.

16. The vacuum pump filtration system according to claim 1, wherein the filtration membrane is hydrophobic.

17. The vacuum pump filtration system according to claim 16, wherein the filtration membrane has a water breakthrough pressure of at least about 8 psi, coupled with a nominal pore size of less than 0.25 µm.

18. A vacuum pump filtration system according to claim 1, wherein said filtration membrane is affixed to a mating surface within the filtration cap element using a pressure sensitive adhesive.

19. A vacuum pump filtration system according to claim 1, comprising one or more visual indicators configured to communicate one or more operational parameters to the user.

20. A vacuum pump filtration system according to claim 19, wherein the one or more visual indicators comprise one or more parameters selected from the group consisting of operational status of the vacuum pump, charge status of a battery supply, remaining operational life of the filter element, vacuum level within the chamber, and compliance with medical directives for use of the vacuum pump filtration system.

21. A method of creating a region of negative pressure on a portion of a subject's body, comprising:
    providing the vacuum pump filtration system according to claim 1;
    inserting the wall portion of the pump housing element through the aperture of the evacuation enclosure;
    engaging the mating surface of the filtration cap element with the receiving surface of the pump housing element from within the interior of the evacuation enclosure such that the edge portion of the evacuation enclosure forming the aperture is entrapped between the pump housing element and the filtration cap element to form the integral pump/filter unit, thereby forming a substantially airtight seal of the aperture;
    placing the evacuation enclosure on a portion of a subject to form the chamber having an interior volume formed between the subject's body and the evacuation enclosure; and
    energizing the vacuum pump to remove air from the interior volume within the chamber, wherein the air being removed passes through the filter membrane prior to reaching the vacuum pump.

22. A method of assembling a vacuum pump filtration system comprising:
    providing the vacuum pump filtration system according to claim 1;
    inserting the wall portion of the pump housing element through the aperture of the evacuation enclosure; and
    engaging the mating surface of the filtration cap element with the receiving surface of the pump housing element from within the interior of the evacuation enclosure such that the edge portion of the evacuation enclosure forming the aperture is entrapped between the pump housing element and the filtration cap element to form the integral pump/filter unit, thereby forming a substantially airtight seal of the aperture.

* * * * *